US012582368B2

(12) United States Patent
Stanchev et al.

(10) Patent No.: US 12,582,368 B2
(45) Date of Patent: Mar. 24, 2026

(54) SETUP FOR SCOUT SCANS IN A RADIATION THERAPY SYSTEM

(71) Applicant: VARIAN MEDICAL SYSTEMS, INC., Palo Alto, CA (US)

(72) Inventors: Sevelin Stanchev, Las Vegas, NV (US); Stephen Thompson, Pacific Grove, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 333 days.

(21) Appl. No.: 17/881,593

(22) Filed: Aug. 4, 2022

(65) Prior Publication Data

US 2024/0041416 A1      Feb. 8, 2024

(51) Int. Cl.
| | |
|---|---|
| *A61B 6/00* | (2024.01) |
| *A61B 6/04* | (2006.01) |
| *A61B 6/46* | (2024.01) |
| *A61N 5/10* | (2006.01) |

(52) U.S. Cl.
CPC ............ *A61B 6/488* (2013.01); *A61B 6/0407* (2013.01); *A61B 6/44* (2013.01); *A61B 6/465* (2013.01); *A61B 6/469* (2013.01); *A61N 5/1081* (2013.01)

(58) Field of Classification Search
CPC ... A61B 6/0407; A61B 6/0487; A61B 6/0478; A61B 6/0492; A61B 6/461; A61B 6/465
See application file for complete search history.

(56) References Cited

U.S. PATENT DOCUMENTS

| | | | |
|---|---|---|---|
| 7,502,445 | B2 | 3/2009 | Shi et al. |
| 11,110,300 | B2 | 9/2021 | Van Heteren et al. |
| 12,053,650 | B2 | 8/2024 | Vojan et al. |
| 2014/0098932 | A1 | 4/2014 | Profio et al. |
| 2015/0297166 | A1 | 10/2015 | Goto et al. |
| 2016/0174930 | A1* | 6/2016 | Braun ................. A61B 6/0407 378/205 |
| 2017/0143291 | A1 | 5/2017 | Guntzer et al. |
| 2020/0030634 | A1 | 1/2020 | Van Heteren et al. |
| 2021/0244376 | A1 | 8/2021 | Buelow et al. |
| 2022/0061781 | A1 | 3/2022 | Zhao |
| 2022/0203134 | A1 | 6/2022 | Givehchi et al. |
| 2023/0154594 | A1* | 5/2023 | Dutta Choudhury .. G16H 30/40 382/128 |

OTHER PUBLICATIONS

Non-Published Commonly Owned U.S. Patent Application, Filed on Aug. 4, 2022, 44 pages.

* cited by examiner

*Primary Examiner* — David J Makiya
*Assistant Examiner* — Miya Downing
(74) *Attorney, Agent, or Firm* — SU IP CONSULTING

(57) ABSTRACT

A method for a radiation therapy system comprises: causing a graphical representation of a movable support couch of the X-ray imaging system to be displayed, wherein the graphical representation includes one or more reference markers that each correspond to a respective physical feature of the movable support couch; receiving a first user input that includes a first position indicator that corresponds to a first boundary of an X-ray imaging region; and generating an X-ray image of the X-ray imaging region, wherein a first edge of the X-ray image corresponds to the first boundary.

21 Claims, 10 Drawing Sheets

100

101     102          102     101

103

107

105

REMOTE CONTROL
CONSOLE
110

106

GUI 600

601

608

602

614

610

611

611

610

610

612

612

610

610

613

613

610

610

610

609

Longitudinal

Lateral

SETUP FOR SCOUT SCANS IN A RADIATION THERAPY SYSTEM

CROSS REFERENCE TO RELATED APPLICATION

The present application is related in subject matter to patent application Ser. No. 17/881,592.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy performed on the planning target volume spares the surrounding normal tissue from receiving doses above specified tolerances, thereby mini-mizing risk of damage to healthy tissue. Prior to the delivery of radiation therapy, an imaging system is typically employed to provide a three-dimensional image of the target tissue and surrounding area. For example, a treatment plan-ning scan is often performed via computed tomography (CT) to generate the three-dimensional image. From such imag-ing, the size and mass of the target tissue can be estimated, a planning target volume determined, and an appropriate treatment plan generated.

To define the scan range of the treatment planning scan and ensure that the region of interest of patient anatomy is captured in the treatment planning scan, one or more scout scans of the patient (also referred to as topograms) are performed immediately prior to the treatment planning scan. A topogram is a 2-dimensional X-ray image of a region of interest that is acquired using a CT scanner, but is not used to reconstruct a three-dimensional region of slices.

With a conventional CT scanner, the patient is loaded on the couch, and the user adjusts the couch position so that the region of interest is located within the field of view of the CT scanner. Then, the user sets the boundaries for one or more scout scans, such as a side view and a plan view of the region of interest, and the one or more scout scans of the patient anatomy are acquired. Visual analysis of these scout scans reveals the approximate location of the target tissue within the area of interest and, based on that location, a suitable treatment planning scan can be acquired of the target tissue and surrounding patient anatomy.

Prior to the scout scan, the location of the target tissue within a region of interest is unknown to the user of the CT scanner. Therefore, it is important that the region of interest is centered as much as possible in the portion of patient anatomy that is imaged by the CT scanner prior to acquisi-tion of the scout scan. Otherwise, the target tissue may be partially or completely outside the portion of patient anatomy that is imaged in the scout scan. When that is the case, additional scout scans must be acquired, which is time-consuming and results in additional radiation dosing of the patient. Further, when the scout scan is performed in conjunction with patient immobilization, a scanning process of longer duration can be uncomfortable for the patient.

One drawback to a conventional CT scanner is that, prior to obtaining a scout image, centering a region of interest of patient anatomy relative to the CT scanner coordinates can be difficult and time consuming. Because anatomical dimen-sions and radiation therapy targets vary widely from patient to patient, a particular region of interest, such as the head, abdomen, thorax, etc., cannot be centered for a scout scan acquisition using a predetermined couch position. Instead, for any given patient, the user must manually fine-tune couch longitudinal positions until the region of interest appears to be centered in the field of view of the CT scanner for the scout image. Such an approach can require multiple iterations of couch repositioning or additional scout-scan views, which consumes valuable scanner time and may result in patient discomfort or additional radiation exposure. Further, such an approach is subject to human error, which can require additional scout scan acquisitions when the target tissue within the region of interest is partially or completely outside the field of view of an acquired scout scan.

Accordingly, there is a need in the art for techniques to facilitate the setup of a radiation therapy system for a scout scans.

SUMMARY

In accordance with at least some embodiments, a com-puted tomography (CT) imaging system is configured to facilitate boundary selection for a CT scout scan and accu-rate positioning of a patient for the scout scan. Specifically, during patient setup, a graphical user interface (GUI) of the CT imaging system displays a graphical representation of a movable support couch of the CT imaging system, where the graphical representation includes one or more reference markers that each correspond to a different physical feature of the movable support couch. Thus, when the patient is positioned on the movable support couch, the user can visually identify the location of a region of interest of patient anatomy relative to a particular physical feature of the movable support couch. Then, via the GUI, the user defines boundaries of the scout scan relative to a reference marker in the GUI that corresponds to that particular physical feature. In some embodiments, the CT imaging system is incorporated in a radiation therapy system. In such embodi-ments, a treatment-delivering X-ray source of the radiation therapy system and an imaging X-ray source of the CT imaging system can both be configured to rotate about a common isocenter.

In accordance with at least some embodiments, a com-puter-implemented method for an X-ray imaging system includes: causing a graphical representation of a movable support couch of the X-ray imaging system to be displayed, wherein the graphical representation includes one or more reference markers that each correspond to a respective physical feature of the movable support couch; receiving a first user input that includes a first position indicator that corresponds to a first boundary of an X-ray imaging region; and generating an X-ray image of the X-ray imaging region, wherein a first edge of the X-ray image corresponds to the first boundary.

In accordance with at least some embodiments, an X-ray imaging system includes: a movable support couch; an imaging X-ray source configured to direct imaging X-rays to an X-ray imaging region proximate the movable support couch; and a processor. The processor is configured to perform the steps of: causing a graphical representation of the movable support couch to be displayed, wherein the graphical representation includes one or more reference markers that each correspond to a respective physical feature of the movable support couch; receiving a first user input that includes a first position indicator that corresponds to a first boundary of the X-ray imaging region; and generating an X-ray image of the X-ray imaging region, wherein a first edge of the X-ray image corresponds to the first boundary.

Further embodiments include a non-transitory computer-readable storage medium comprising instructions that cause a computer system to carry out one or more of the above methods, as well as a computer system configured to carry out one or more of the above methods.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
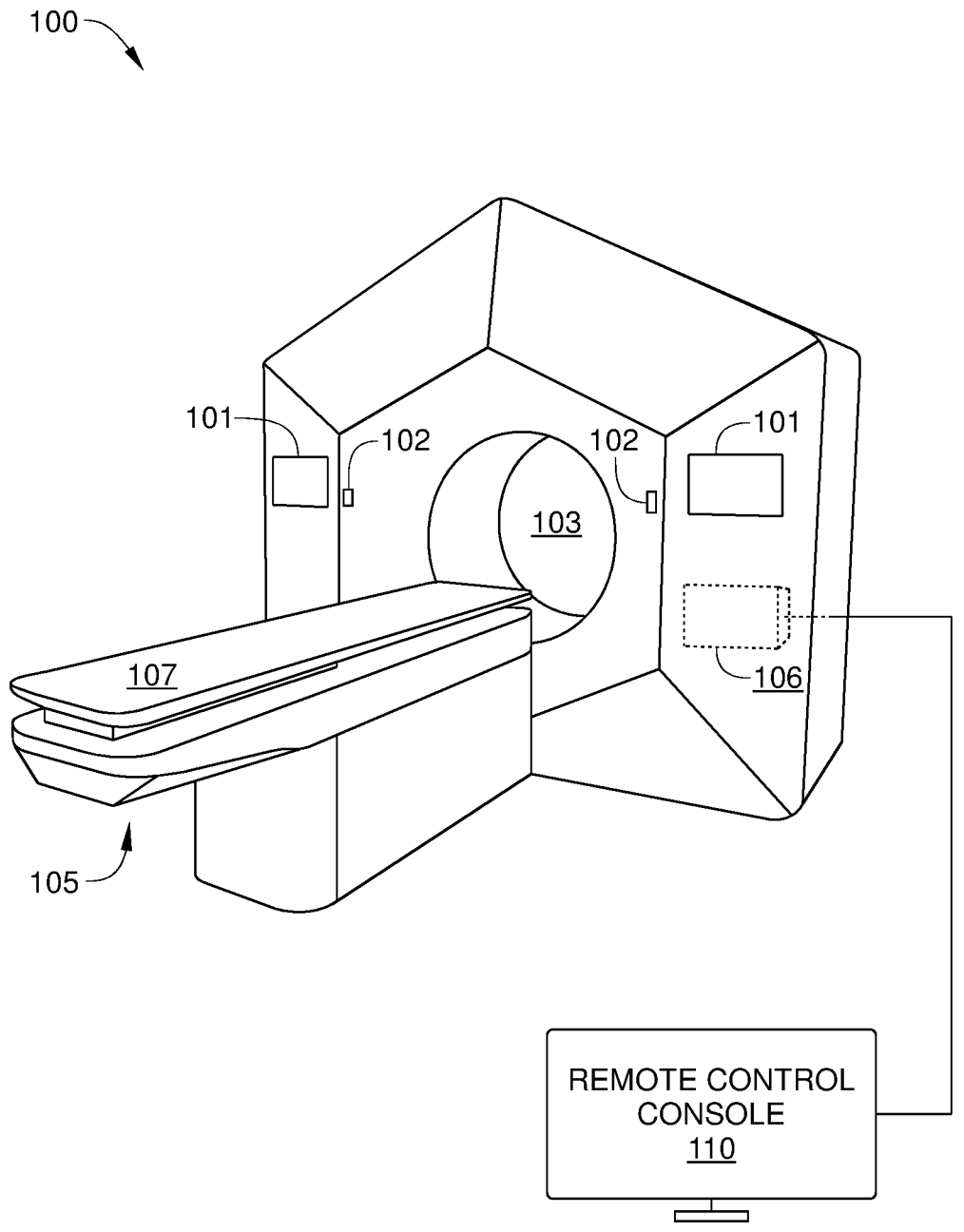
FIG. 1 is a perspective view of a radiation therapy system, according to various embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

System Overview

FIG. 1 is a perspective view of a radiation therapy (RT) system 100, according to various embodiments. RT system 100 is configured to image patient anatomy surrounding a planning target volume, such as a tumor, and reconstruct a digital volume of the patient anatomy that includes the planning target volume. In some embodiments, radiation therapy system 100 performs such imaging via a cone-beam computed tomography (CBCT) process using one or more imagers incorporated in radiation therapy system 100, such as one or more kilovolt (kV) X-ray imagers. In some embodiments, RT system 100 is a radiation system configured to detect inter-fraction motion using X-ray imaging techniques. In some embodiments, RT system 100 is a radiation system configured to detect intra-fraction motion in near-real time using X-ray imaging techniques. Thus, in such embodiments, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, RT system 100 is described herein configured with a circular gantry. In other embodiments, RT system 100 can be configured with a C-gantry capable of infinite rotation via a slip ring connection.

Generally, RT system 100 is capable of kV imaging of a target volume, to generate treatment planning image information (such as a treatment planning scan) and/or to generate images during a radiation therapy treatment fraction. Thus, in some embodiments, RT system 100 can be employed in addition to or instead of a treatment planning computed tomography imager. Further, in some embodiments, RT system is configured to image a target volume immediately prior to and/or during application of an MV treatment beam, so that an image-guided radiation therapy (IGRT) process and/or an intensity-modulated radiation therapy (IMRT) process can be performed using X-ray imaging. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location.

Figure 2:
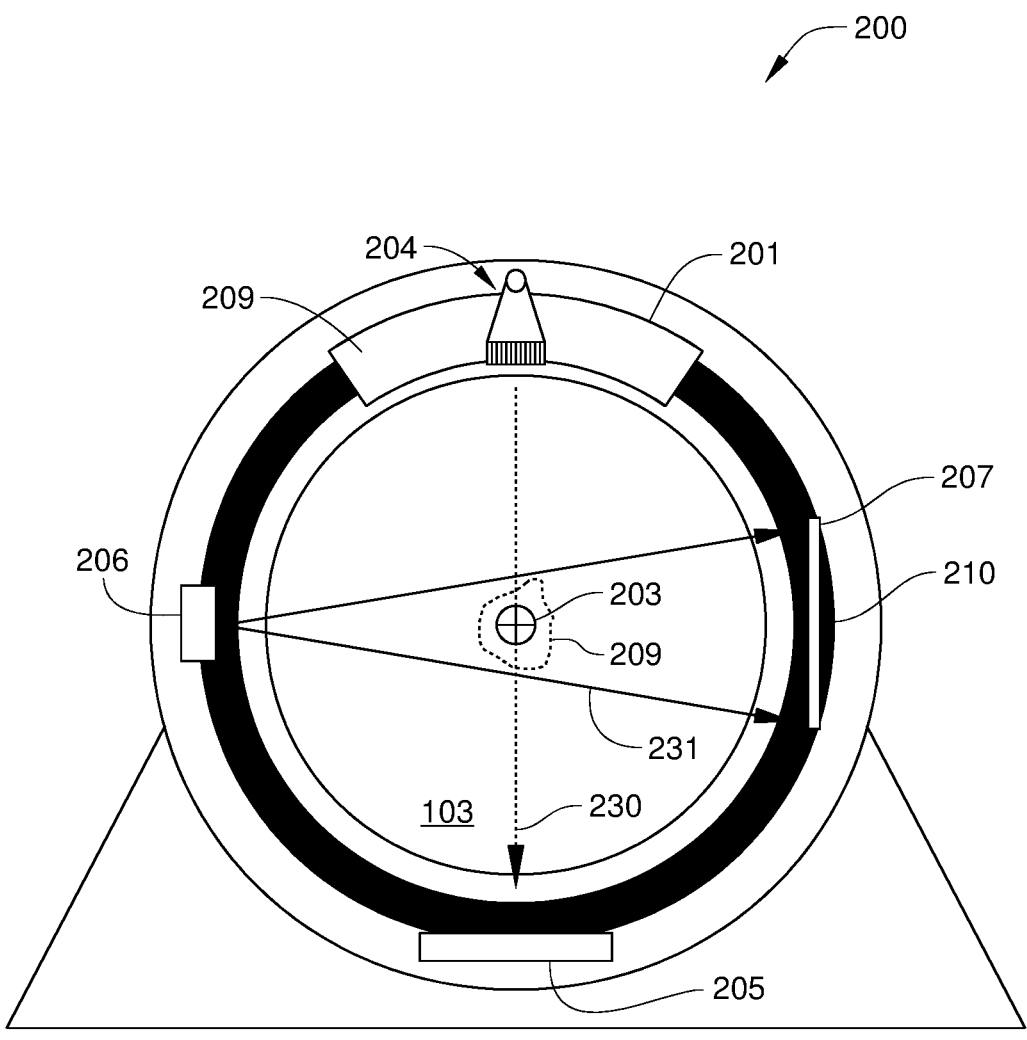
FIG. 2 schematically illustrates a drive stand and gantry of the radiation therapy system of FIG. 2, according to various embodiments.

FIG. 2 schematically illustrates a drive stand 200 and gantry 210 of RT system 100, according to various embodiments. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT system 100, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT system 100, gantry 220 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons, protons, and/or other heavy charged particles, ultra-high dose rate X-rays (e.g., for FLASH radiotherapy) or microbeams for microbeam radiation therapy) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In some embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can be generated. In some embodiments, CBCT can be employed to generate treatment planning images. Additionally or alternatively, in some embodiments, CBCT is employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape. Alternatively, or additionally, in some embodiments, partial-data reconstruction is performed by RT system 100 during portions of an IGRT or IMRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. One such embodiment is illustrated in FIG. 3.

Figure 3:
FIG. 3 schematically illustrates a drive stand and a gantry of the radiation therapy system of FIG. 2, according to various embodiments.
Figure 3:
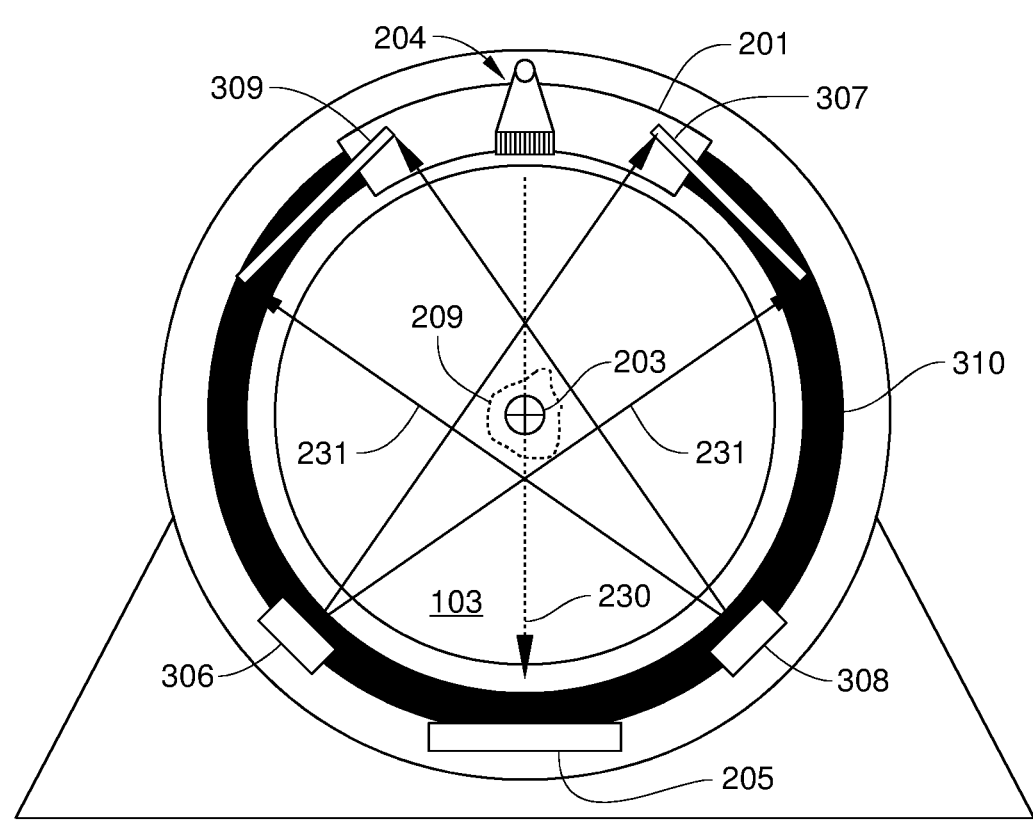

FIG. 3 schematically illustrates a drive stand 300 and gantry 310 of RT system 100, according to various embodiments. Drive stand 300 and gantry 310 are substantially similar in configuration to drive stand 200 and gantry 210 in FIG. 2, except that the components of RT system 100 that are mounted on gantry 310 include a first imaging X-ray source 306, a first X-ray imager 307, a second imaging X-ray source 308, and a second X-ray imager 309. In such embodiments, the inclusion of multiple X-ray imagers in RT system 100 facilitates the generation of projection images (for reconstructing the target volume) over a shorter image acquisition arc. For instance, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 207 (or by first x-ray imager 307 and second X-ray imager 309) are used to construct imaging data for a digital volume of patient anatomy within a 3D region that includes the target volume. Alternatively or additionally, such projection images can be used to update portions of existing imaging data for the digital volume corresponding to the 3D region. One embodiment of such a digital volume is described below in conjunction with FIG. 4.

Figure 4:
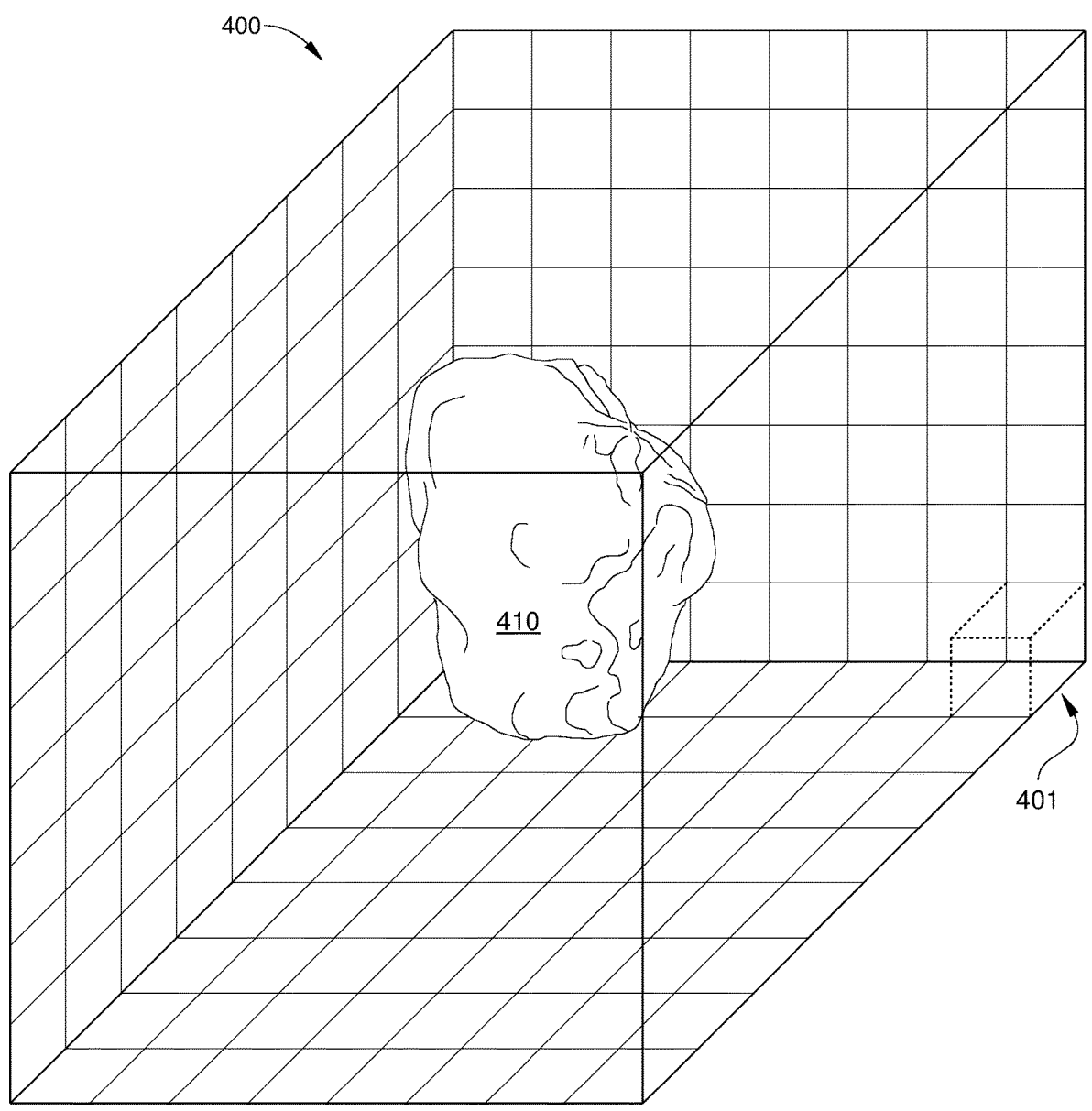
FIG. 4 schematically illustrates a digital volume that is constructed based on projection images of an anatomical region generated by one or more X-ray imagers included in the radiation therapy system of FIG. 2, according to various embodiments.

FIG. 4 schematically illustrates a digital volume 400 that is constructed based on projection images of an anatomical region generated by one or more X-ray imagers included in RT system 100, according to various embodiments. For example, in some embodiments, the projection images can be generated by a single X-ray imager, such as X-ray imager 207, and in other embodiments the projection images can be generated by multiple X-ray imagers, such as first x-ray imager 307 and second X-ray imager 309.

Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the GTV, CTV, or the PTV for a particular treatment. The GTV depicts the position and extent of the gross tumor, for example what can be seen or imaged; the CTV includes the GTV and an additional margin for sub-clinical disease spread, which is generally not imagable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 400.

Generally, image information associated with each voxel 401 of digital volume 400 is constructed via projection images generated by single or multiple X-ray imagers via a CBCT process. For example, such a CBCT process can be a treatment planning scan of a region of interest of patient anatomy. As noted previously, a scout scan of the region of interest is first performed to define the scan range of the treatment planning scan and ensure that the PTV is captured in the treatment planning scan.

Setup for Treatment Planning Scans

According to various embodiments, a CT imaging system is configured to facilitate boundary selection for a scout scan and accurate positioning of a patient for the scout scan. During patient setup, a graphical user interface (GUI) of the CT imaging system displays a graphical representation of a movable support couch of the CT imaging system, where the graphical representation includes one or more reference markers that each correspond to a different physical feature of the movable support couch. One such embodiment is described below in conjunction with FIGS. 5-6C.

Figure 5:
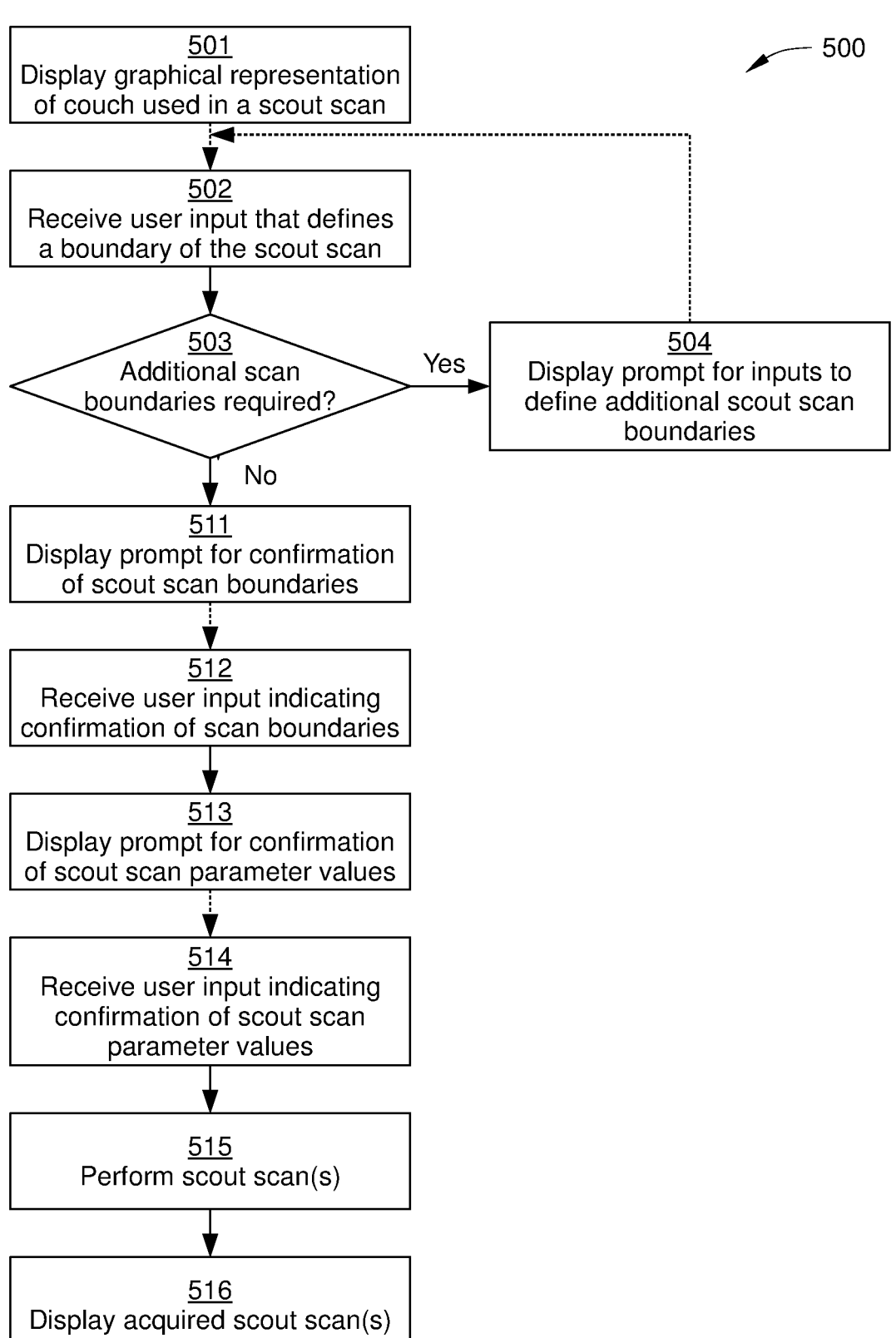
FIG. 5 sets forth a flowchart of a method for the setup and performance of computed tomography scout scans with an X-ray imaging system, according to one or more embodiments.
Figure 6A:
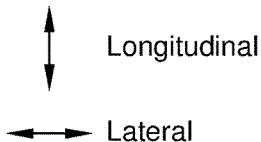
FIGS. 6A, 6B, and 6C schematically illustrate a graphical user interface of the radiation therapy system of FIG. 2 displayed by a remote display screen and/or a treatment room display screen at certain steps of the method of FIG. 5, according to various embodiments
Figure 6B:
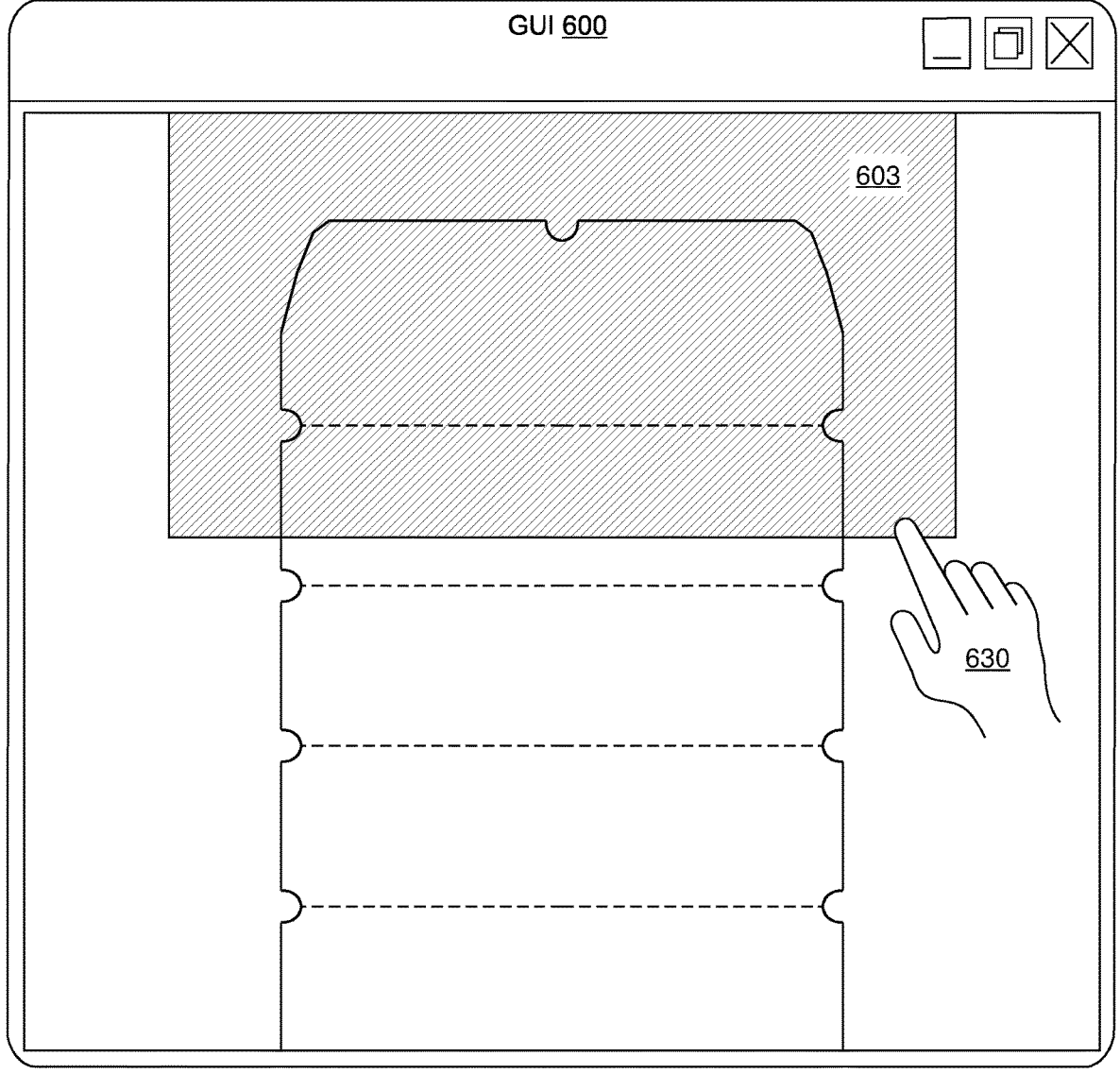
Figure 6C:
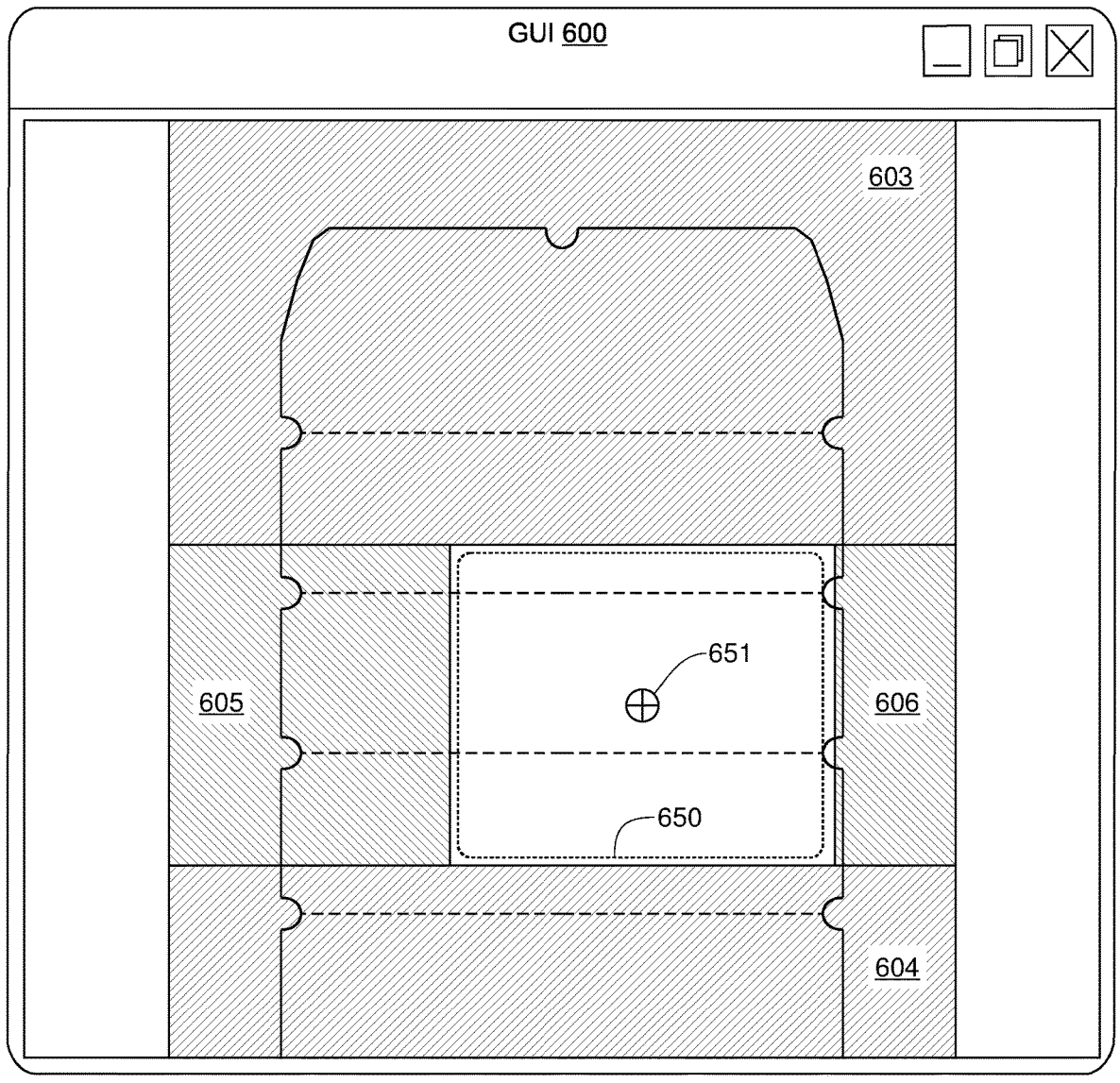

FIG. 5 sets forth a flowchart of a method 500 for the setup and performance of CT scout scans with an X-ray system, according to one or more embodiments. Method 500 may include one or more operations, functions, or actions as illustrated by one or more of blocks 501-516. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although method 500 is described in conjunction with RT system 100 and FIGS. 1-4, persons skilled in the art will understand that any suitably configured X-ray imaging system is within the scope of the present embodiments. FIGS. 6A-6C schematically illustrate a graphical user interface (GUI) 600 of RT system 100 displayed by a remote display screen and/or a treatment room display screen at certain steps of method 500, according to various embodiments.

Method 500 is generally performed in response to a particular patient receiving a diagnosis that necessitates radiation therapy and thus the generation of a radiation therapy treatment plan. As noted previously, such a treatment plan is typically generated based on a digital volume, such as digital volume 400, that includes a target volume, such as target volume 410. The digital volume is reconstructed based on imaging information obtained via a treatment planning scan that is performed using an X-ray imaging system, such as the onboard X-ray imaging of RT system 100. According to various embodiments, the scan range of the treatment planning scan is defined based on one or more scout scans of the patient that are performed, as described below, immediately prior to the treatment planning scan. In some embodiments, prior to method 500, the patient is positioned on couch 107, and couch 107 is moved to a zero position. In some instances, the patient is positioned in conjunction with prescribed immobilization, so that a suitable patient position is maintained during the treatment planning scan. Alternatively or additionally, in some instances, the patient is administered with a prescribed contrast medium, which can be administered intravenously or ingested.

Method 500 begins at step 501, where RT system 100 displays a GUI 600 at a display screen, as shown in FIG. 6A. For example, in some embodiments, the display screen is a display screen associated with a treatment room display, such as touchscreen 101. Alternatively or additionally, in some embodiments, GUI 600 displays GUI 600 at remote control console 110. In either case, GUI 600 includes a graphical representation 601 of a movable support couch that is employed in the scout scan performed in method 500, such as couch 107.

In some embodiments, graphical representation 601 includes one or more reference markers 610 that each correspond to a different respective physical feature of the movable support couch. For example, in the embodiment illustrated in FIG. 6A, when a patient is positioned face-up and head-first on couch 107, graphical representation 601 includes one or more reference markers 611 that correspond to first longitudinal position indicators formed on couch 107, one or more reference markers 612 that correspond to second longitudinal position indicators formed on couch 107, one or more reference markers 613 that correspond to third longitudinal position indicators formed on couch 107, and so on. For example, the first, second, and/or third longitudinal position indicators can be physical features formed on the edges of couch 107, such as notches or projections. Alternatively or additionally, in some embodiments, the first, second, and/or third longitudinal position indicators can be graduations or other markings formed on one or more surfaces of couch 107 at different longitudinal positions, such as stripes, numerals, and/or other markings.

In such embodiments, such longitudinal position indicators visually indicate to the user a predetermined longitudinal position on couch 107. Thus, in an embodiment, the first longitudinal position indicators (which correspond to reference markers 611) visually indicate to the user viewing the patient a first predetermined longitudinal position on couch 107; the second longitudinal position indicators (which correspond to reference markers 612) visually indicate to the user a second predetermined longitudinal position on couch 107; the third longitudinal position indicators (which correspond to reference markers 613) indicate to the user a third predetermined longitudinal position on couch 107; and so on. Consequently, reference markers 611 display, in GUI 600, the location of the first predetermined longitudinal position on couch 107; reference markers 612 display, in GUI 600, the location of the second predetermined longitudinal position on couch 107; and reference markers 613 display, in GUI 600, the location of the third predetermined longitudinal position on couch 107. As a result, when a patient is positioned on couch 107 and a region of interest of patient anatomy occupies a particular position on couch 107, a user can visually determine a location in graphical representation 601 that corresponds to the particular longitudinal (head-to-toe) position that is occupied on couch 107 by the region of interest.

In the embodiment illustrated in FIG. 6A, multiple reference markers 610 correspond to a specific longitudinal position along a longitudinal axis 608 (such as the major axis) of couch 107. For example, one of reference markers 611 corresponds to a left-hand edge of couch 107 and another reference marker 611 corresponds to a right-hand edge of couch 107, but both of reference markers 611 correspond to the same longitudinal position. Similarly, one of reference markers 612 corresponds to a left-hand edge of couch 107 and another reference marker 612 corresponds to a right-hand edge of couch 107, but both of reference markers 612 correspond to the same longitudinal position.

In the embodiment illustrated in FIG. 6A, reference markers 610 correspond to physical features of a movable support couch that are positioned at different longitudinal locations along longitudinal axis 608 of couch 107. Additionally or alternatively, in some embodiments, some or all of reference markers 610 correspond to physical features of a movable support couch that are positioned at different locations along a different axis of couch 107, such as a lateral axis 609. Thus, in such embodiments, a user can visually determine a location in graphical representation 601 that corresponds to the particular lateral (left-to-right) position occupied on couch 107 by a region of interest of patient anatomy. For example, in one such embodiment, a reference marker 614 corresponds to a physical feature of couch 107 that indicates a lateral position on couch 107.

Alternatively or additionally, in some embodiments, graphical representation 601 includes a pictogram 602 of at least a portion of a perimeter of couch 107. In such embodiments, pictogram 602 provides additional two-dimensional visual cues to the user that can further facilitate the translation of the actual position on couch 107 that is occupied by a region of interest to a location within GUI 600. In some embodiments, to better facilitate the visual cues provided by pictogram 602, pictogram is a scaled diagram of some or all of the perimeter of couch 107. That is, in such embodiments, the two dimensions of pictogram 602 are reduced equally from the actual size of couch 107, so that pictogram 602 is an accurate visual representation of the geometry of some or all of the perimeter of couch 107.

In step 502, RT system 100 receives a user input that defines a boundary of the scout scan to be performed, for example via GIU 600, as shown in FIG. 6B. In some embodiments, the user input can be received when the user makes an appropriate selection with GUI 600. For example, in some embodiments, the user positions or moves a position indicator 603 to a location that corresponds to a boundary of an X-ray imaging region associated with the scout scan to be performed. For example, the user may position indicator 603 via a mouse click or finger tap 630.

In embodiments in which a patient is positioned face-up and head-first on couch 107 and a boundary of a frontal (or plan-view) scout scan is being defined, the position indicator 603 can be one of a first longitudinal boundary marker (such as a superior boundary marker), a second longitudinal boundary marker (such as an inferior boundary marker), a first lateral boundary marker (such as a left boundary marker), or a second lateral boundary marker (such as a right boundary marker). Alternatively or additionally, in embodiments in which a patient is positioned face-up and head-first on couch 107 and a boundary of a side-view scout scan is being defined, the position indicator 603 can be one of a first longitudinal boundary marker (such as a superior boundary marker), a second longitudinal boundary marker (such as an inferior boundary marker), a first vertical boundary marker (such as an anterior boundary marker), or a second vertical boundary marker (such as a posterior boundary marker).

Position indicator 603 indicates a boundary of an X-ray imaging region associated with the scout scan to be performed. Thus, in the embodiment, the hash-marked region corresponds to a region that lies outside of the scout scan to be performed. In the embodiment illustrated in FIG. 6B, position indicator 603 serves as a superior boundary marker.

In step 503, in response to the user input received in step 502, RT system 100 determines whether additional scout scan boundaries are required to perform the scout scan. For example, in some embodiments, four scout scan boundaries are needed to define an X-ray imaging region of the scout scan. In some embodiments, two scout scan boundaries are needed to define an X-ray imaging region of the scout scan. In some embodiments, the boundaries for multiple scout scans may be required.

When RT system 100 determines that additional scout scan boundaries are required, method 500 proceeds to step 504; when RT system 100 determines no additional scout scan boundaries are required, method 500 proceeds to step 511. In step 504, RT system 100 displays a user prompt for additional inputs that define additional scout scan boundaries.

In step 511, RT system 100 displays a prompt for user confirmation of the scout scan boundaries currently defined by the user, for example by the position indicators 603, 604, 605, and 606 shown in FIG. 6C. Step 511 is performed in response to RT system 100 determining that no additional scout scan boundaries are required to perform the scout scan. In FIG. 6C, the scout scan boundaries of an X-ray imaging region 650 of the scout scan are defined by multiple position indicators 603, 604, 605, and 606. In the embodiment illustrated in FIG. 6C, assuming the patient is positioned head first and supine and the scout scan is acquired with a downward view, position indicator 603 defines a superior boundary of the scout scan, position indicator 604 defines an inferior boundary of the scout scan, position indicator 605 defines a left boundary of the scout scan, and position indicator 606 defines a right boundary of the scout scan. Alternatively, in the embodiment illustrated in FIG. 6C, when the patient is positioned differently (e.g. head first and face-down, feet first and supine, etc.) and/or the scout scan is acquired with an upward view, position indicator 603, position indicator 604, position indicator 605, and/or position indicator 606 can each define different boundaries. For example, assuming the patient is positioned head first and supine and an upward view is employed to generate the scout scan, position indicator 603 defines a superior boundary of the scout scan, position indicator 604 defines an inferior boundary of the scout scan, position indicator 605 defines a right boundary of the scout scan, and position indicator 606 defines a left boundary of the scout scan. In some embodiments, RT system 100 further displays an indicator of an imaging isocenter 651 that corresponds to X-ray imaging region 650. For example, in some embodiments, imaging isocenter 651 corresponds to isocenter 203 in FIG. 2. In such embodiments, couch 107 is repositioned prior to the scout scan being performed, so that imaging isocenter 651 is located relative to couch 107 as shown in FIG. 6C.

In the embodiment illustrated in FIG. 6C, four position indicators are employed to define X-ray imaging region 650. In other embodiments, two position indicators can be employed to define an X-ray imaging region associated with a scout scan. For example, in one such embodiment, a first position indicator (e.g., position indicator 603) defines a superior boundary of the scout scan and a second position indicator (e.g., position indicator 604) defines an inferior boundary of the scout scan. Alternatively, in another such embodiments, a first position indicator (e.g., position indicator 605) defines a left boundary of the scout scan and a second position indicator (e.g., position indicator 606) defines a right boundary of the scout scan.

In step 512, RT system 100 receives a user input indicating confirmation of the scout scan boundaries, for example via GUI 600. In step 513, in response to receiving the user confirmation in step 512, RT system 100 displays a prompt for user confirmation of other scout scan parameter values, such as specific values for scanning energy (kV), tube current (mAs), exposure time, exposure/dose (mSv), and the like. In step 514, RT system 100 receives a user input indicating confirmation of the specified scout scan parameter values, for example via GUI 600.

In step 515, RT system 100 performs the scout scan based on the scout scan boundaries confirmed in step 512 and the scout scan parameters confirmed in step 514. In some embodiments, RT system 100 performs multiple scout scans, such as two scout scans having orthogonal fields of view. For example, in one such embodiment, RT system 100 performs a frontal (or plan-view) scout scan and a side-view scout scan. In some embodiments, in step 515, couch 107 is moved to a specified imaging location for each scout scan performed. Typically, each scout scan is a single X-ray projection image that is acquired by an imaging system of RT system 100. In some embodiments, each of the one or more edges of such X-ray projection images corresponds to a different boundary of the scout scan, where each boundary is defined by a position indicator that is positioned based on user inputs as described above.

In step 516, RT system 100 displays the scout scans acquired in step 515.

Exemplary Computing Device

Figure 7:
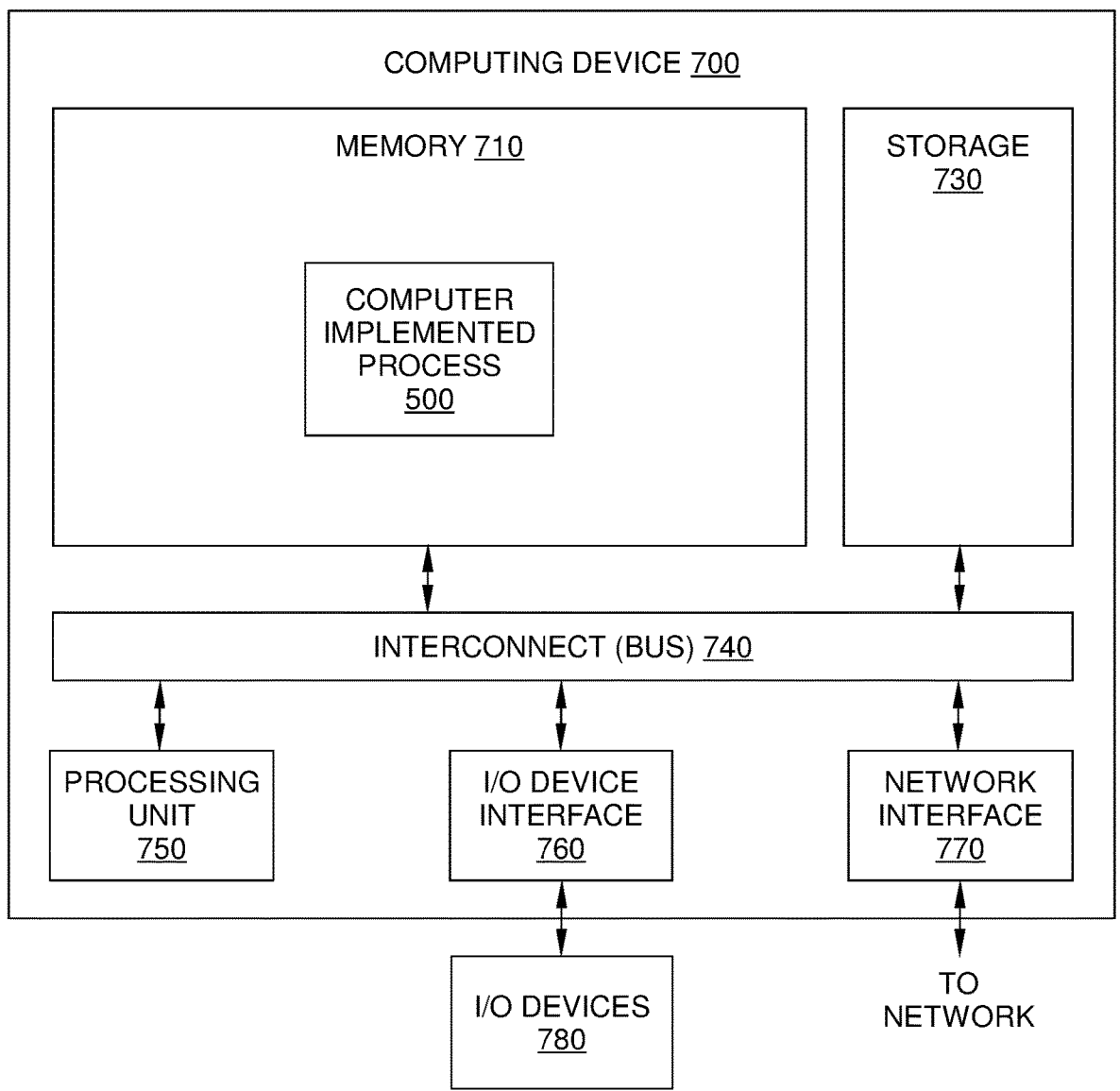
FIG. 7 is an illustration of a computing device configured to perform various embodiments of the present disclosure.

FIG. 7 is an illustration of computing device 700 configured to perform various embodiments of the present disclosure. Thus, in some embodiments, computing device 700 is implemented as or associated with image acquisition and treatment control computer 106 and/or remote control console 110. Computing device 700 may be a desktop computer, a laptop computer, a smart phone, or any other type of computing device suitable for practicing one or more embodiments of the present disclosure. In operation, computing device 700 is configured to execute instructions associated with computer-implemented method 500 as described herein. It is noted that the computing device described herein is illustrative and that any other technically feasible configurations fall within the scope of the present disclosure.

As shown, computing device 700 includes, without limitation, an interconnect (bus) 740 that connects a processing unit 750, an input/output (I/O) device interface 760 coupled to input/output (I/O) devices 780, memory 710, a storage 730, and a network interface 770. Processing unit 750 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 750 may be any technically feasible hardware unit capable of processing data and/or executing software applications, including computer-implemented method 500.

I/O devices 780 may include devices capable of providing input, such as a keyboard, a mouse, a touch-sensitive screen, and so forth, as well as devices capable of providing output, such as a display device and the like. Additionally, I/O devices 780 may include devices capable of both receiving input and providing output, such as a touchscreen, a universal serial bus (USB) port, and so forth. I/O devices 780 may be configured to receive various types of input from an end-user of computing device 700, and to also provide various types of output to the end-user of computing device 700, such as displayed digital images or digital videos. In some embodiments, one or more of I/O devices 780 are configured to couple computing device 700 to a network.

Memory 710 may include a random access memory (RAM) module, a flash memory unit, or any other type of memory unit or combination thereof. Processing unit 750, I/O device interface 760, and network interface 770 are configured to read data from and write data to memory 710. Memory 710 includes various software programs that can be executed by processor 750 and application data associated with said software programs, including computer-implemented method 500.

Figure 8:
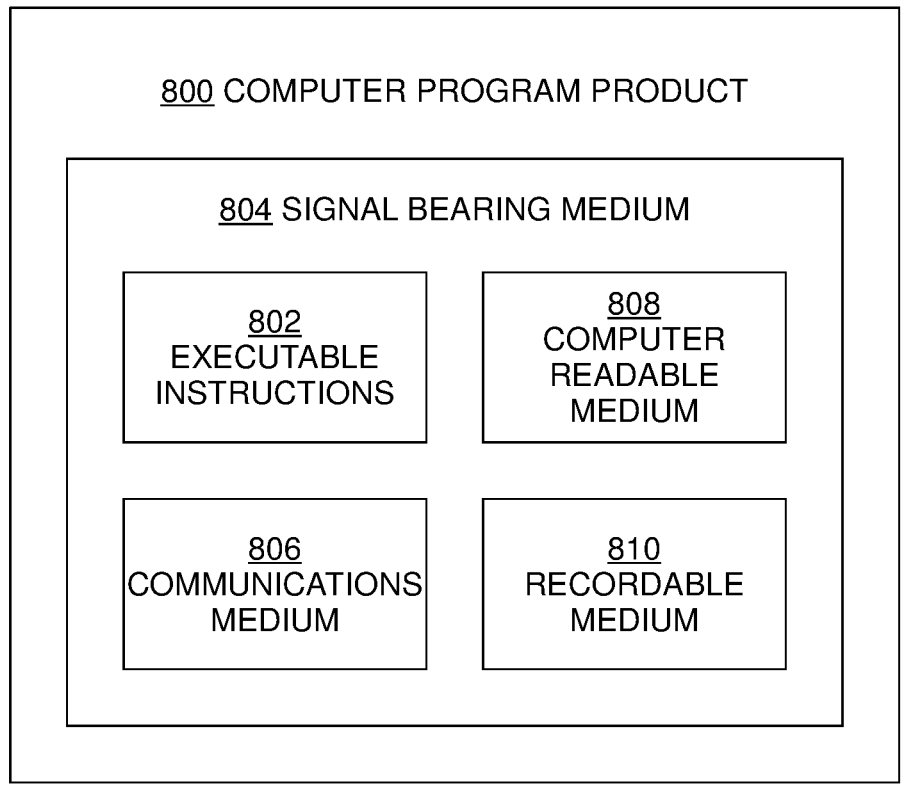
FIG. 8 is a block diagram of an illustrative embodiment of a computer program product for implementing one or more embodiments of the present disclosure.

FIG. 8 is a block diagram of an illustrative embodiment of a computer program product 800 for implementing a method for segmenting an image, according to one or more embodiments of the present disclosure. Computer program product 800 may include a signal bearing medium 804. Signal bearing medium 804 may include one or more sets of executable instructions 802 that, when executed by, for example, a processor of a computing device, may provide at least the functionality described above with respect to FIGS. 1-7.

In some implementations, signal bearing medium 804 may encompass a non-transitory computer readable medium 808, such as, but not limited to, a hard disk drive, a Compact Disc (CD), a Digital Video Disk (DVD), a digital tape, memory, etc. In some implementations, signal bearing medium 804 may encompass a recordable medium 810, such as, but not limited to, memory, read/write (R/W) CDs, R/W DVDs, etc. In some implementations, signal bearing medium 804 may encompass a communications medium 806, such as, but not limited to, a digital and/or an analog communication medium (e.g., a fiber optic cable, a waveguide, a wired communications link, a wireless communication link, etc.). Computer program product 800 may be recorded on non-transitory computer readable medium 808 or another similar recordable medium 810.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method for an X-ray imaging system, the method comprising:

causing a graphical representation of a movable support couch of the X-ray imaging system to be displayed in a graphical user interface associated with the X-ray imaging system, wherein the graphical representation includes one or more reference markers that each correspond to a respective physical feature of the movable support couch;

receiving a first user input that includes a first position indicator that corresponds to a first region of the graphical user interface, wherein an edge of the first region defines a first boundary of an X-ray imaging region;

prior to generating an X-ray image of the X-ray imaging region, causing a graphical representation of an imaging isocenter's indicator to be displayed in conjunction with the graphical representation of the movable support couch in the graphical user interface; and generating the X-ray image of the X-ray imaging region, wherein a first edge of the X-ray image corresponds to the first boundary.

2. The computer-implemented method of claim 1, wherein receiving the first user input comprises receiving the first user input via the graphical user interface.

3. The computer-implemented method of claim 1, wherein the graphical representation comprises a pictogram of at least a portion of a perimeter of the movable support couch.

4. The computer-implemented method of claim 1, wherein the graphical representation comprises a scaled diagram of at least a portion of the movable support couch.

5. The computer-implemented method of claim 4, wherein the scaled diagram includes at least a portion of a perimeter of the movable couch.

6. The computer-implemented method of claim 1, wherein each of the one or more reference markers corresponds to a respective longitudinal position on the movable support couch.

7. The computer-implemented method of claim 1, wherein a first reference marker of the one or more reference markers corresponds to a left-hand edge of the movable support couch, and a second reference marker of the one or more reference markers corresponds to a right-hand edge of the movable support couch.

8. The computer-implemented method of claim 1, further comprising receiving a second user input that includes a second position indicator that corresponds to a second region of the graphical user interface, wherein an edge of the second region defines a second boundary of the X-ray imaging region.

9. The computer-implemented method of claim 8, wherein the first boundary comprises a first longitudinal boundary of the X-ray imaging region and the second boundary comprises a second longitudinal boundary of the X-ray imaging region.

10. The computer-implemented method of claim 8, wherein the first boundary comprises a first lateral boundary of the X-ray imaging region and the second boundary comprises a second lateral boundary of the X-ray imaging region.

11. The computer-implemented method of claim 1, further comprising, causing the movable support couch to be repositioned prior to generating the X-ray image of the X-ray imaging region.

12. The computer-implemented method of claim 1, further comprising:

displaying the first boundary; and receiving a third user input to confirm the first boundary.

13. An X-ray imaging system comprising:

a movable support couch;

an imaging X-ray source configured to direct imaging X-rays to an X-ray imaging region proximate the movable support couch; and a processor configured to perform the steps of:

causing a graphical representation of the movable support couch to be displayed in a graphical user interface associated with the X-ray imaging system, wherein the graphical representation includes one or more reference markers that each correspond to a respective physical feature of the movable support couch;

receiving a first user input that includes a first position indicator that corresponds to a first region of the graphical user interface, wherein an edge of the first region defines a first boundary of the X-ray imaging region;

prior to generating an X-ray image of the X-ray imaging region, causing a graphical representation of an imaging isocenter's indicator to be displayed in conjunction with the graphical representation of the movable support couch; and generating the X-ray image of the X-ray imaging region, wherein a first edge of the X-ray image corresponds to the first boundary.

14. The X-ray imaging system of claim 13, further comprising a treatment-delivering X-ray source configured to rotate about an isocenter of the X-ray imaging system and direct treatment X-rays to a target volume proximate the X-ray imaging region.

15. The X-ray imaging system of claim 14, wherein the imaging X-ray source is configured to rotate about the isocenter.

16. The X-ray imaging system of claim 13, wherein each physical feature is visible to a user positioned at a position controller of the movable support couch when a patient is positioned on the movable support couch.

17. The X-ray imaging system of claim 13, wherein receiving the first user input comprises receiving the first user input via the graphical user interface.

18. The X-ray imaging system of claim 13, wherein the graphical representation comprises a pictogram of at least a portion of a perimeter of the movable support couch.

19. The X-ray imaging system of claim 13, wherein the graphical representation comprises a scaled diagram of at least a portion of the movable support couch.

20. The X-ray imaging system of claim 19, wherein the scaled diagram includes at least a portion of a perimeter of the movable couch.

21. The X-ray imaging system of claim 13, wherein each of the one or more reference markers corresponds to a respective longitudinal position on the movable support couch.

* * * * *